(12) United States Patent
Korn et al.

(10) Patent No.: US 9,206,109 B2
(45) Date of Patent: Dec. 8, 2015

(54) METHOD OF STABILIZING POLYMERIZABLE COMPOUNDS

(71) Applicant: BASF SE, Ludwigshafen (DE)

(72) Inventors: Tobias Johannes Korn, Ludwigshafen (DE); Peter Zurowski, Landau (DE); Thorsten Friese, Mannheim (DE); Sylke Haremza, Neckargemuend (DE); Ulrich Jaeger, Roemerberg (DE); Steffen Rissel, Kirchheim (DE); Volker Schliephake, Schifferstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/104,165

(22) Filed: Dec. 12, 2013

(65) Prior Publication Data

US 2014/0228571 A1 Aug. 14, 2014

Related U.S. Application Data

(60) Provisional application No. 61/739,019, filed on Dec. 19, 2012.

(51) Int. Cl.
*C07C 51/50* (2006.01)
*C07C 67/62* (2006.01)

(52) U.S. Cl.
CPC ............... *C07C 51/50* (2013.01); *C07C 67/62* (2013.01)

(58) Field of Classification Search
None
See application file for complete search history.

(56) References Cited

U.S. PATENT DOCUMENTS

| | | | |
|---|---|---|---|
| 4,507,495 A | 3/1985 | Dougherty et al. | |
| 4,542,231 A | 9/1985 | Dougherty et al. | |
| 4,814,493 A * | 3/1989 | Dougherty et al. | 560/205 |
| 5,198,578 A | 3/1993 | Etzkorn et al. | |
| 2004/0242826 A1 | 12/2004 | Nishimura | |
| 2012/0217444 A1 * | 8/2012 | Liu et al. | 252/400.53 |

FOREIGN PATENT DOCUMENTS

| | | |
|---|---|---|
| DE | 197 34 171 A1 | 2/1999 |
| DE | 697 01 590 T2 | 9/2000 |
| DE | 100 28 582 A1 | 12/2001 |
| DE | 10 2007 004 960 A1 | 7/2008 |
| DE | 10 2008 040 799 A1 | 12/2008 |
| DE | 10 2007 055 086 A1 | 5/2009 |
| DE | 10 2009 027 401 A1 | 2/2010 |
| DE | 10 2008 041 573 A1 | 3/2010 |
| EP | 0 765 856 A1 | 4/1997 |
| EP | 1 015 410 B1 | 4/2002 |
| EP | 1 484 303 A2 | 12/2004 |
| EP | 1 484 308 A1 | 12/2004 |
| EP | 1 484 309 A1 | 12/2004 |
| EP | 1 710 227 A1 | 10/2006 |
| JP | 2001-348359 A | 12/2001 |
| WO | WO 02/35596 A1 | 5/2002 |
| WO | WO 2006/136336 A2 | 12/2006 |
| WO | WO 2007/074044 A1 | 7/2007 |
| WO | WO 2010/012586 A1 | 2/2010 |

* cited by examiner

Primary Examiner — Timothy R Rozof
(74) Attorney, Agent, or Firm — Oblon, McClelland, Maier & Neustadt, L.L.P.

(57) ABSTRACT

In a method of stabilizing acrylic compounds, a liquid phase containing at least one acrylic compound is mixed with at least one metal and at least one ligand. The acrylic compound can be acrylic acid, methacrylic acid, and their respective esters. The metal can be copper, manganese, and cerium. The ligand can be a quinoline compound of formula (I), an N-oxide of a compound of formula (I), 2,2"-bis(2,3-dihydro-3-oxoindolylidene), or an aliphatic y-dentate ligand with y being 2-6 and comprising at least two nitrogen atoms joined by aliphatic or aromatic $C_1$-$C_4$ bridges comprising y-2 further coordinating nitrogen atoms or heteroatoms:

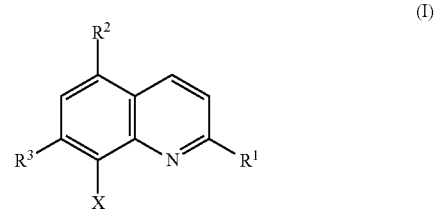

where X is OH, $NH_2$, O—($C_1$-$C_4$)-alkyl, O—C(O)—($C_1$-$C_4$)-alkyl, or O—C(O)-phenyl; $R^1$ is H, or ($C_1$-$C_4$)-alkyl; $R^2$ is H, ($C_1$-$C_4$)-alkyl, Cl, Br, or $SO_3H$; and $R^3$ is H, Cl or Br.

11 Claims, No Drawings

METHOD OF STABILIZING POLYMERIZABLE COMPOUNDS

The invention relates to a method of stabilizing (meth)acrylic acid and (meth)acrylic esters in the liquid phase by addition of a Cu-, Mn- or Ce-comprising polymerization inhibitor, the liquid phases produced when carrying out the method and the use of the Cu-, Mn- or Ce-comprising polymerization inhibitor for stabilizing (meth)acrylic acid and (meth)acrylic esters in the liquid phase.

Acrylic acid, methacrylic acid and esters thereof are important monomers for producing polymers which are used, for example, as adhesives or as superabsorbents. However, a great problem in the preparation and reaction of these compounds is the high tendency to undergo spontaneous polymerization because of the reactive double bonds in these compounds.

In the following, acrylic acid and/or methacrylic acid are referred to as (meth)acrylic acid for short, and the respective esters are referred to as (meth)acrylic esters.

It has been known for a long time that addition of inhibitors (also referred to as retarders) to (meth)acrylic acid and esters thereof in the liquid phase can counter polymerization-promoting influences.

The variety of inhibitors recommended for this purpose in the prior art is virtually unlimited (cf., for example, EP 765 856 A and DE 69 701 590 T2, which acknowledge a small selection from among these inhibitors) and also comprises compounds of the elements copper (cf., for example, JP-A 2001-348359), manganese (cf., for example, U.S. Pat. No. 4,814,493, U.S. Pat. No. 4,542,231, U.S. Pat. No. 4,507,495) and cerium (cf., for example, WO 2002/035596 A).

Although good results are achieved using the known systems, none of the known inhibitors is completely satisfactory. Thus, high costs are incurred by the cleaning of the production plants which is necessary at short intervals, so that the full capacity of the plants cannot be utilized.

It was therefore an object of the invention to provide further polymerization inhibitors which are superior at least in some aspects to the known systems and, in particular, can effectively suppress the tendency of (meth)acrylic acid and esters thereof to polymerize in the liquid phase.

It has been found that complexes of copper, manganese and cerium with specific nitrogen-comprising ligands are particularly suitable as polymerization inhibitors for (meth)acrylic acid and (meth)acrylic esters in the liquid phase.

The invention accordingly provides a method of stabilizing acrylic compounds, wherein a liquid phase comprising at least one acrylic compound selected from the group consisting of acrylic acid, methacrylic acid and the respective esters thereof is admixed with at least one metal selected from the group consisting of copper, manganese and cerium and also at least one ligand selected from the group consisting of
a) quinoline compounds of the formula (I)

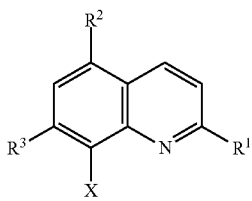

(I)

where the symbols have the following meanings:
X is OH, $NH_2$, $O-C_1-C_4$-alkyl, preferably $OCH_3$, $O-C(O)-C_1-C_4$-alkyl, preferably $O-C(O)-CH_3$, $O-C(O)-C_2H_5$ or $O-C(O)$-phenyl;
$R^1$ is H, or $(C_1-C_4)$-alkyl, preferably methyl;
$R^2$ is H, $C_1-C_4$-alkyl, preferably methyl, Cl, Br or $SO_3H$ and
$R^3$ is H, Cl or Br;
and also N-oxides of compounds of the formula (I),
b) 2,2'-bis(2,3-dihydro-3-oxoindolylidene) and
c) aliphatic y-dentate ligands having y=2-6 and comprising at least two nitrogen atoms and aliphatic or aromatic $C_1-C_4$ bridges comprising y−2 further coordinating nitrogen atoms or heteroatoms.

The invention further provides a liquid phase comprising at least 10% by weight of at least one compound selected from the group consisting of acrylic acid, methacrylic acid and the respective esters thereof and at least one complex comprising at least one metal selected from the group consisting of copper, manganese and cerium and also at least one ligand selected from the group consisting of a) quinoline compounds of the formula (I) and also N-oxides of compounds of the formula (I), b) 2,2'-bis(2,3-dihydro-3-oxoindolylidene), and c) aliphatic y-dentate ligands having y=2-6 and comprising at least two nitrogen atoms joined by aliphatic or aromatic $C_1-C_4$ bridges comprising y−2 further coordinating nitrogen atoms or heteroatoms.

The invention likewise provides for the use of a complex comprising at least one metal selected from the group consisting of copper, manganese and cerium and at least one ligand selected from the group consisting of a) quinoline compounds of the formula (I) and also N-oxides of compounds of the formula (I), b) 2,2'-bis(2,3-dihydro-3-oxoindolylidene), and c) aliphatic y-dentate ligands having y=2-6 and comprising at least two nitrogen atoms joined by aliphatic or aromatic $C_1-C_4$ bridges comprising y−2 further coordinating nitrogen atoms or heteroatoms as polymerization inhibitor for stabilizing acrylic acid, methacrylic acid and/or the respective esters thereof.

The polymerization inhibitors of the invention display, particularly in the case of acrylic acid and methacrylic acid, a significantly stronger inhibiting action than known systems such as phenothiazine.

The at least one ligand used in the method of the invention is preferably selected from the group consisting of a) the quinoline compounds of the formula (I) and also N-oxides of compounds of the formula (I), b) 2,2'-bis(2,3-dihydro-3-oxoindolylidene), and c) aliphatic y-dentate ligands having y=2-6 and comprising at least two nitrogen atoms joined by aliphatic or aromatic $C_1-C_4$ bridges comprising y−2 further coordinating nitrogen atoms or heteroatoms. It is also possible to use any mixtures of the ligands according to the invention.

Among the ligands of group a), preference is given to quinoline compounds of the formula (I) and N-oxides thereof in which the symbols have the following meanings:
X is OH, $NH_2$, $OCH_3$, $O-C(O)CH_3$, $O-C(O)C_2H_5$ or $O-C(O)$phenyl;
$R^1$ is H or $CH_3$;
$R^2$ is H, $CH_3$, $NH_2$, Cl, Br or $SO_3H$ and
$R^3$ is H or Cl.

Particular preference is given to quinoline compounds of the formula (I) and N-oxides thereof in which the symbols have the following meanings:
X is OH or $NH_2$;
$R^1$ is H or $CH_3$;
$R^2$ is H, $CH_3$, Cl or $NH_2$ and
$R^3$ is H.

Particular preference is also given to quinoline compounds of the formula (I) and N-oxides thereof selected from the group consisting of 8-hydroxyquinoline, 8-hydroxy-5-methylquinoline, 5-chloroquinoline-8-yl propionate, 5-chloro-8-hydroxyquinoline, 5,7-dibromo-8-hydroxy-2-methylquinoline, 8-hydroxy-2-methylquinoline (8-hydroxyquinaldine), 8-acetoxyquinoline, 8-aminoquinoline, 8-amino-2-methylquinoline (8-aminoquinaldine), 5-amino-8-hydroxyquinoline and 8-hydroxyquinoline N-oxide.

Very particular preference is given to quinoline compounds of the formula (I) and N-oxides thereof selected from the group consisting of 8-hydroxyquinoline, 5-chloro-8-hydroxyquinoline, 5-amino-8-hydroxyquinoline and 8-hydroxyquinoline N-oxide.

Special preference is given to 8-hydroxyquinoline.

A likewise preferred ligand is 2,2'-bis(2,3-dihydro-3-oxoindolylidene) (indigo) of group b).

Preference is likewise given to ligands of the group c) which consists of aliphatic y-dentate ligands having y=2-6 and comprising at least two nitrogen atoms joined by aliphatic or aromatic $C_1$-$C_4$ bridges comprising y−2 further coordinating nitrogen atoms or heteroatoms.

These compounds are, for example, those of the general formula (II)

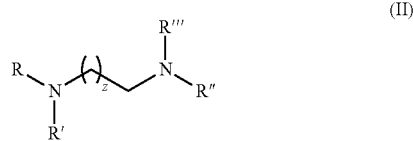

where z is an integer in the range from 1 to 3 and the radicals R, R', R" and R'" can all be identical or different and are each H or $C_1$-$C_4$-alkyl. Preference is given to the radicals R, R', R" and R'" all being identical and each being hydrogen or methyl. In the case of aliphatic carbon bridges, these can be interrupted by further nitrogen atoms or heteroatoms such as oxygen or sulfur, so as to form carbon bridges having from 1 to 4 carbon atoms. These carbon bridges can be either linear or else branched or cyclic. Preference is given to linear carbon bridges having from 1 to 4 carbon atoms, preferably 2 or 3 carbon atoms, with particular preference being given to ethyl groups. As an alternative, the carbon bridge can also be interrupted by an aromatic comprising nitrogen atoms or heteroatoms such as oxygen or sulfur. For example, the compounds are in this case azines, i.e. heterocyclic compounds having from 1 to 4 nitrogen atoms in the ring, or oxazines, i.e. heterocycles having one oxygen atom and one nitrogen atom in the ring in each case.

Preferred representatives of group c) are bidentate to tetradentate ligands having at least two nitrogen atoms and from 0 to two further coordinating nitrogen-comprising or heteroaromatic $C_1$-$C_4$ bridges.

Preferred representatives of this group are 1,1,4,7,10,10-hexamethyltriethylenetetramine, N,N,N',N",N"-pentamethyldiethylenetriamine (Lupragen® N301 from BASF SE, Ludwigshafen), N,N,N',N'-tetramethylethane-1,2-diamine, N,N,N',N'-tetramethylpropane-1,3-diamine, 1,3,5-tris(dimethylaminopropyl)sym-hexahydrotriazine (Lupragen® N600 from BASF SE, Ludwigshafen), bis(2-dimethylaminoethyl) ether (Lupragen® N205 from BASF SE, Ludwigshafen) and tris[2-(dimethylamino)ethyl]amine.

Among this group, particular preference is given to 1,1,4,7,10,10-hexamethyltriethylenetetramine, 1,3,5-tris(dimethylaminopropyl)sym-hexahydrotriazine (Lupragen® N600 from BASF SE, Ludwigshafen) and bis(2-dimethylaminoethyl) ether (Lupragen® N205 from BASF SE, Ludwigshafen)

According to the invention, preference is given to using from 0.01 molar ppm to 5 mol %, particularly 0.1 molar ppm to 3 mol %, very particularly 0.5 molar ppm to 1 mol %, in particular from 2 molar ppm to 0.1 mol %, of the ligand, based on the acrylic compound.

According to the invention, the complex used as polymerization inhibitor comprises at least one, preferably precisely one, metal selected from the group consisting of copper, manganese and cerium, in particular copper(II), copper(I), manganese(II) and cerium(III). Preference is given to copper (II), copper(I) and manganese(II). Particular preference is given to copper(II) and copper(I). Copper(II) is very preferred.

The metal is used as salt; suitable metal salts are, for example, copper(II) phenoxide, copper(II) acetylacetonate, copper(II) gluconate, copper(II) tartrate, copper(II) acetate, copper(II) formate, copper(II) nitrate, copper(II) hydroxide, copper(II) sulfate, copper(II) carbonate, copper(II) naphthenate, copper(II) acrylate, copper(II) halides such as copper(II) chloride, copper(II) salicylate, copper(II) sulfonate, copper (II) propionate, copper(II) octanoate, which can each also have water of hydration. Further suitable salts are copper(I) compounds such as CuCl, CuCN, CuI, CuBr, Cu(I) acetate, $Cu_2SO_4$, $Cu_2O$ and CuCN, and also salts of complex copper (I) anions such as $Cu(CN)_4^{3-}$ or complex copper(I) cations such as $Cu(NH_3)_4^+$. Copper(I) salts are less suitable as additive to aqueous liquid phases since the $Cu^+$ in these tends to disproportionate. The corresponding manganese and cerium salts are also suitable. Cu(II) acetate is particularly preferred.

In principle, the metal compound, in particular copper compound, to be added to the liquid phase can be dispersed in finely divided form in the liquid phase (e.g. as finely divided solid or as dispersed fine liquid droplets (optionally a solution comprising the metal compound)).

However, according to the invention, the metal compound, in particular copper compound, to be added to the liquid phase is dissolved in the liquid phase. The liquid phase can itself be a solution or a liquid phase in a system consisting of a plurality of liquid phases.

In a preferred embodiment of the process of the invention, the complex used according to the invention as polymerization inhibitor is added as such to the liquid phase.

In a further preferred embodiment of the process of the invention, metal salt, in particular copper salt, and ligand are added to the liquid phase and the complex used according to the invention as polymerization inhibitor is formed in the liquid phase.

Based on the molar amount of acrylic compound, in particular acrylic acid, comprised in the liquid phase, the at least one metal from the group consisting of Cu, Mn and Ce will be added in the process of the invention in such amounts that the content G of metal, in particular Cu, in the liquid phase, based on the molar amount of acrylic compound, in particular acrylic acid, comprised therein is generally from 0.01 molar ppm to 5 mol % or up to 3 mol %. This means that in the process of the invention G can be from 0.05 molar ppm to 2 mol %, or from 0.01 molar ppm to 1 mol %, or from 1 molar ppm to 5000 molar ppm, or from 3 molar ppm to 3000 molar ppm, or 5 molar ppm to 1000 molar ppm, or from 10 molar ppm to 800 molar ppm, or from 20 molar ppm to 500 molar ppm, or from 30 molar ppm to 300 molar ppm, or from 40 molar ppm to 200 molar ppm, or from 50 molar ppm to 100 molar ppm, or from 0.1 molar ppm to 10 molar ppm.

The preferred molar ratio of metal to ligand is generally from 1:1 to 1:10, preferably from 1:1 to 1:6, particularly preferably from 1:1 to 1:4, very particularly 1:2.

Metal salt and ligand of the complex can, for example, be added as pure substance or preferably in solution to the liquid phase. As solvent, it is possible to use, for example, the liquid phase itself or the acrylic compound, in particular acrylic acid (in general an acrylic acid having a high purity), or the same solvent in which the acrylic compound, in particular acrylic acid, is dissolved in the liquid phase, or a constituent or a mixture of a plurality of constituents of this solvent. If the complex is added as pure salt, the polymorphic forms thereof can also be used. Polymorphy is the capability of chemical compounds of the same empirical formula to occur in various crystal structures (see Epple, Biometalle and Biomaterialien, Teubner-Verlag, 1$^{st}$ edition 2003, page 6). Thus, for example, the α-, β- and γ forms of the copper(II) complex with 8-hydroxyquinoline can be used.

The acrylic compounds stabilized according to the invention are (meth)acrylic acid and esters of the two acids. Preferred esters are linear or branched alkyl esters, preferably having from 1 to 20 carbon atoms. Examples of preferred acrylates are methyl acrylate, ethyl acrylate, n-butyl acrylate, tert-butyl acrylate and 2-ethylhexyl acrylate. Particular preference is given to acrylic acid and methacrylic acid. Acrylic acid is especially preferred.

In the process of the invention, the liquid phase will frequently comprise at least 20% by weight, or at least 30% by weight, or at least 40% by weight, or at least 50% by weight, or at least 60% by weight, or at least 70% by weight, or at least 80% by weight, or at least 90% by weight, or at least 95% by weight, or at least 98% by weight, of acrylic compound (in each case based on the weight of the liquid phase).

The method of the invention is particularly suitable for stabilizing acrylic acid. The acrylic acid can be prepared, for example, by heterogeneously catalyzed partial oxidation of a $C_3$ precursor compound (e.g. propylene, propane, acrolein, propionaldehyde, propionic acid, propanol and/or glycerol) in the gas phase (cf., for example, WO 2010/012586, U.S. Pat. No. 5,198,578, EP-A 1 710 227, EP-A 1 015 410, EP-A 1 484303, EP-A 1 484 308, EP-A 1 484 309, US-A 2004/0242826, WO 2006/136336, DE-A 10 028 582 and WO 2007/074044).

According to the invention, the polymerization inhibitors composed of metal and ligand are preferably used in places where the (meth)acrylic acid or the respective ester thereof is subject to a risk of polymerization due to, for example, high purity, long residence time and/or high temperature. The method of the invention is therefore suitable for stabilization of (meth)acrylic acid or the respective esters thereof present in a liquid phase both during storage and during handling in a process. The latter case applies particularly when the liquid phase is subjected to a thermal separation process which does not involve crystallization (the temperatures which occur are generally above 50° C., usually above 60° C. or 70° C., or above 90° C. or 110° C.). These are generally thermal separation processes in which gaseous (ascending) and liquid (descending) streams or two liquid streams are conveyed in countercurrent in separation columns comprising separation-active internals, with heat transfer and mass transfer which ultimately bring the separation desired in the separation column as a result of the gradient existing between the streams. Examples of such thermal separation processes which do not involve crystallization are rectification, azotropic rectification, extraction, desorption, stripping, distillation, azeotropic distillation and adsorption. It goes without saying that the method of the invention for inhibition of polymerization is suitable even when the liquid phase is subjected to a thermal separation process involving crystallization.

For the present purposes, the term "thermal separation processes" indicates that heat has to be introduced into or withdrawn from the system in order to achieve the desired separating action (cf. DE-A 10 2008 041573 and DE-A 10 2008 8040799).

The liquid phase to be treated in a process can have had the at least one complex to be added according to the invention added to it right from the beginning of the thermal separation process (i.e. it can be treated according to the invention before introduction into the thermal process). Of course, the at least one complex can also be added during the course of the thermal separation process (e.g. in the case of a rectification, dissolved in the reflux liquid, or in the case of an absorption dissolved in the absorption medium, or in the case of a fractional condensation dissolved in the reflux liquid, or in the case of direct cooling of the product gas mixture from the heterogeneously catalyzed partial gas-phase oxidation of the $C_3$ precursor compound, dissolved in the quenching liquid used for direct cooling).

Of course, the at least one complex to be added according to the invention to the liquid phase does not have to be the only inhibitor system added to the liquid phase. Rather, the liquid phase can additionally comprise one or more added inhibitors from the group comprising nitroxyl radicals (also referred to as N-oxyl radicals) (e.g. those disclosed in DE-A 19734171, e.g. 4-hydroxy-2,2,6,6-tetramethylpiperidine-1-oxyl or 1,4-dihydroxy-2,2,6,6-tetramethylpiperidine), phenothiazines such as dibenzo-1,4-thiazine (phenothiazine), phenolic compounds such as hydroquinone, 2,4-dimethyl-6-t-butylphenol and hydroquinone monomethyl ether, molecular oxygen, p-phenylenediamine (e.g. that disclosed in DE-A 19734171), organic nitroso compounds such as 4-nitrosophenol (and the others disclosed in DE-A 19734171), methylene blue and all other inhibitors disclosed, for example, in EP-A 765856. Preferred inhibitors can be added to the liquid phase in appropriate amounts as are indicated and recommended in the present text for the at least one complex to be added to the liquid phase.

When carrying out thermal separation processes which do not involve crystallization on liquid phases treated according to the invention in separation columns comprising built-in separation-active internals (e.g. separation trays such as dual-flow trays), it is possible for, for example, air or nitrogen-enriched air (lean air) to be passed through the separation column (e.g. a rectification column or absorption column) as source of molecular oxygen to provide an additional inhibiting measure, as is practiced, for example, in DE-A 102009027401 and in DE-A 102007004960.

An advantageous inhibitor combination for stabilizing the rectification of the acrylic acid-comprising absorbate A* carried out in the rectification column K30 in DE-A 102009027401 (in addition to the air flowing through the rectification column K30) is, based on the respective amount of acrylic acid to be stabilized (to be inhibited), for example from 0.1 to 3 molar ppm of Cu (added in the form of at least one Cu-comprising compound (preferably Cu(II) di-n-butyldithiocarbamate) and from 50 to 1000 ppm by weight of phenothiazine, preferably from 0.2 to 2 molar ppm of Cu and from 100 to 500 ppm by weight of phenothiazine and particularly preferably from 0.3 to 1 molar ppm of Cu and from 200 to 400 ppm by weight of phenothiazine. The introduction of the inhibitor into the rectification column K30 is advantageously effected as a solution in the reflux liquid or as a solution in the absorbate A* fed to the rectification column K30.

Corrosion tests have shown that the DIN material 1.4571 is a suitable and fully satisfactory corrosion-resistant apparatus material for liquid phases inhibited according to the invention, in which the metal is copper.

The invention is illustrated by the following examples without being restricted thereby.

EXAMPLES

1. Production of Liquid Phases Admixed with Various Polymerization Inhibitors and Also of Differently Inhibited Comparative Liquid Phases As described in DE-A 10 2007 055 086, freshly prepared pure acrylic acid which, based on its weight, had been polymerization-inhibited by means of 200 ppm by weight of methoxyphenol (MEHQ) was freed of MEHQ by double, successive distillation under reduced pressure (1000 Pa).

The purity of the pure acrylic acid distillate produced in this way was >99.8% by weight, with a total aldehyde and ketone content of <5 ppm by weight and a diacrylic acid content of <1 ppm by weight.

A part of the pure acrylic acid distillate was divided into identical samples of 1 ml.

Another part was used to produce various stock solutions in which, for example, various amounts of different polymerization inhibitors were dissolved.

Samples taken from the stock solutions were diluted with the amount required in each case of the pure acrylic distillate and diluted as desired with the dilutions of the various 1 ml samples. The doped samples were subsequently preserved by freezing.

2. Preparation of Cu(II) Oxinate from Various Copper Salts

Mixtures of 8-hydroxyquinoline with various copper compounds were prepared and examined by means of thin layer chromatography (TLC).
TLC eluent: acetonitrile: 0.05M $KH_2PO_4$ (pH 3.0) 6:4
TLC material: TLC silica gel 60 RP-18 F254
The following copper compounds were used:
1. Copper(II) acetate monohydrate
2. Copper(I) chloride
3. Copper(II) 2,4-pentanedionate
4. Copper(II) acetylacetonate
5. Cu(I) acetate
6. Cu(II) gluconate Procedure:

An 8 mmol/l solution of 8-hydroxyquinoline in acrylic acid was prepared. Solutions having a concentration of 4 mmol/l were prepared analogously from the copper compounds. 0.5 ml of the 8-hydroxyquinoline solution was in each case mixed with 0.5 ml of copper salt solution and mixed. These solutions were examined by means of TLC. In the case of all the compounds used, the desired copper(II) oxine was formed.

3. Examination of the Tendency of Samples of Various Liquid Phases to Polymerize To examine the polymerization tendency of the respective doped sample, this was liquefied again and an HPLC vial (transparent vessel having a capacity of 1.5 ml) was in each case charged with 0.5 ml of the respective sample under air and subsequently tightly closed by means of a crimped cap. Immediately after they had been produced, up to six vials charged as described were in each case hung in a holder made for this purpose and left in a convection drying oven at a temperature of 120° C. while the holder rotated at six revolutions per minute in order to ensure complete mixing in the vials (the liquid contents of the respective vial came into contact with the crimped cap six times per minute). The time T to complete polymerization of the respective sample in the vial concerned was then measured. For this purpose, the samples in the vials in the drying oven were monitored by means of a video camera (maximum film running time was 720 minutes) and the video film was subsequently evaluated visually.

Each experiment was repeated three times and the associated values for T were averaged arithmetically. The resulting means t (in minutes) for the various samples, including their associated relevant contents of constituents other than acrylic acid, are listed below (the amounts are in each case based on the amount of acrylic acid comprised in the respective sample).

TABLE 1

Stabilization of acrylic acid using Cu(II) acetate and various ligands

| Ligand | Cu salt | t** |
|---|---|---|
| Without stabilizer | | 24 |
| 0.05 mmol/l of phenothiazine | | 144 |
| 0.05 mmol/l of Cu(II) acetate* | | 47 |
| 0.10 mmol/l of 8-hydroxyquinoline | | 30 |
| 0.10 mmol/l of 8-hydroxy-5-methylquinoline | | 29 |
| 0.10 mmol/l of 5,7-dibromo-8-(benzoyloxy)-2-methylquinoline | | 29 |
| 0.10 mmol/l of 5-chloroquinolin-8-yl propionate | | 34 |
| 0.10 mmol/l of 8-acetoxyquinoline | | 31 |
| 0.10 mmol/l of 8-hydroxyquinoline-5-sulfonic acid | | 29 |
| 0.10 mmol/l of 8-aminoquinoline | | 24 |
| 0.10 mmol/l of 8-aminoquinaldine | | 22 |
| 0.10 mmol/l of 8-amino-5-chloro-6-methoxyquinoline | | 23 |
| 0.10 mmol/l of 8-hydroxyquinoline N-oxide | | 33 |
| 0.10 mmol/l of 5-amino-8-hydroxyquinoline | | 22 |
| 0.10 mmol/l of Lupragen ® N205 | | 25 |
| 0.10 mmol/l of Lupragen ® N301 | | 23 |
| 0.10 mmol/l of Lupragen ® N600 | | 24 |
| 0.10 mmol/l of 1,1,4,7,10,10-hexamethylene-triethylenetetramine | | 20 |
| 0.10 mmol/l of indigo | | 33 |
| 0.05 mmol/l of phenothiazine | +0.05 mmol/l of Cu(II) acetate* | 147 |

TABLE 1-continued

Stabilization of acrylic acid using Cu(II) acetate and various ligands

| Ligand | Cu salt | t** |
|---|---|---|
| 0.10 mmol/l of 8-hydroxyquinoline | +0.05 mmol/l of Cu(II) acetate* | >700 |
| 0.10 mmol/l of 8-hydroxy-5-methylquinoline | +0.05 mmol/l of Cu(II) acetate* | 504 |
| 0.10 mmol/l of 5,7-dibromo-8-(benzoyloxy)-2-methylquinoline | +0.05 mmol/l of Cu(II) acetate* | 284 |
| 0.10 mmol/l of 5-chloroquinolin-8-yl propionate | +0.05 mmol/l of Cu(II) acetate* | 529 |
| 0.10 mmol/l 5-chloro-8-hydroxyquinoline | +0.05 mmol/l of Cu(II) acetate* | >700 |
| 0.10 mmol/l of 5,7-dibromo-8-hydroxy-2-methylquinoline | +0.05 mmol/l of Cu(II) acetate* | 301 |
| 0.10 mmol/l of 8-acetoxyquinoline | +0.05 mmol/l of Cu(II) acetate* | 590 |
| 0.10 mmol/l of 8-hydroxyquinoline-5-sulfonic acid | +0.05 mmol/l of Cu(II) acetate* | 418 |
| 0.10 mmol/l of 8-aminoquinoline | +0.05 mmol/l of Cu(II) acetate* | 538 |
| 0.10 mmol/l of 8-aminoquinaldine | +0.05 mmol/l of Cu(II) acetate* | 531 |
| 0.10 mmol/l of 8-amino-5-chloro-6-methoxyquinoline | +0.05 mmol/l of Cu(II) acetate* | 198 |
| 0.10 mmol/l of 8-hydroxyquinoline N-oxide | +0.05 mmol/l of Cu(II) acetate* | >700 |
| 0.10 mmol/l of 5-amino-8-hydroxyquinoline | +0.05 mmol/l of Cu(II) acetate* | >700 |
| 0.10 mmol/l of Lupragen ® N205 | +0.05 mmol/l of Cu(II) acetate* | 213 |
| 0.10 mmol/l of Lupragen ® N301 | +0.05 mmol/l of Cu(II) acetate* | 253 |
| 0.10 mmol/l of Lupragen ® N600 | +0.05 mmol/l of Cu(II) acetate* | 524 |
| 0.10 mmol/l of 1,1,4,7,10,10-hexamethylene-triethylenetetramine | +0.05 mmol/l of Cu(II) acetate* | 436 |
| 0.10 mmol/l of indigo | +0.05 mmol/l of Cu(II)acetate* | 397 |

*as monohydrate
**t denotes the time in minutes to polymerization

TABLE 2

Stabilization of acrylic acid using 8-hydroxyquinoline complexes of various metal salts

| Metal salt | Ligand | t** |
|---|---|---|
|  | 0.05 mmol/l of phenothiazine | 143 |
|  | 0.10 mmol/l of 8-hydroxy-quinoline | 30 |
| 0.05 mmol/l of Cu(I) acetate |  | 51 |
| 0.05 mmol/l of Cu(II) acetate* |  | 44 |
| 0.05 mmol/l of Mn(II) acetate |  | 429 |
| 0.05 mmol/l of Mn(III) acetate* |  | 25 |
| 0.05 mmol/l of Co(II) acetate |  | 21 |
| 0.05 mmol/l of Ce(III) acetate* |  | 430 |
| 0.05 mmol/l of Ni(II) acetylacetonate |  | 28 |
| 0.05 mmol/l of Cu(I) acetate | +0.10 mmol/l of 8-hydroxy-quinoline | 461 |
| 0.05 mmol/l of Cu(II) acetate* | +0.10 mmol/l of 8-hydroxy-quinoline | >700 |
| 0.05 mmol/l of Mn(II) acetate | +0.10 mmol/l of 8-hydroxy-quinoline | >700 |
| 0.05 mmol/l of Mn(III) acetate* | +0.10 mmol/l of 8-hydroxy-quinoline | >700 |
| 0.05 mmol/l of Ce(III) acetate* | +0.10 mmol/l of 8-hydroxy-quinoline | >700 |

*as monohydrate
**t denotes the time in minutes to polymerization

TABLE 3

Dependence of the stabilization of acrylic acid on the molar ratio of Cu(II) to ligands

| Cu(II) acetate* concentration in mmol/l | Concentration [mmol/l]/ligand | | t** |
|---|---|---|---|
| 0.025 | 0.050 | 8-hydroxyquinoline | 244 |
| 0.025 | 0.100 | 8-hydroxyquinoline | 287 |
| 0.050 | 0.100 | 8-hydroxyquinoline | >700 |
| 0.025 | 0.200 | 8-hydroxyquinoline | 490 |
| 0.050 | 0.200 | 8-hydroxyquinoline | >700 |
| 0.025 | 0.050 | indigo | 61 |
| 0.025 | 0.100 | indigo | 101 |
| 0.050 | 0.100 | indigo | 360 |
| 0.025 | 0.200 | indigo | 511 |
| 0.050 | 0.200 | indigo | >700 |
| 0.050 | 0.050 | Lupragen ® N 205 | 101 |
| 0.050 | 0.100 | Lupragen ® N 205 | 213 |
| 0.050 | 0.200 | Lupragen ® N 205 | 530 |
| 0.025 | 0.050 | Lupragen ® N 301 | 76 |
| 0.025 | 0.100 | Lupragen ® N 301 | 143 |
| 0.050 | 0.100 | Lupragen ® N 301 | 253 |
| 0.025 | 0.200 | Lupragen ® N 301 | 298 |
| 0.050 | 0.200 | Lupragen ® N 301 | 552 |
| 0.050 | 0.400 | Lupragen ® N 301 | >700 |
| 0.050 | 0.050 | Lupragen ® N 600 | 148 |
| 0.050 | 0.100 | Lupragen ® N 600 | 524 |
| 0.050 | 0.200 | Lupragen ® N 600 | >700 |
| 0.050 | 0.050 | 1,1,4,7,10,10-hexamethyl-triethylenetetramine | 148 |

TABLE 3-continued

Dependence of the stabilization of acrylic acid on the molar ratio of Cu(II) to ligands

| Cu(II) acetate* concentration in mmol/l | Concentration [mmol/l]/ligand | | t** |
|---|---|---|---|
| 0.050 | 0.100 | 1,1,4,7,10,10-hexamethyl-triethylenetetramine | 524 |
| 0.050 | 0.200 | 1,1,4,7,10,10-hexamethyl-triethylenetetramine | >700 |

*as monohydrate
**t denotes the time in minutes to polymerization

TABLE 4

Stabilization of methacrylic acid

| Stabilizer | t** |
|---|---|
| 0.050 mmol/l of phenothiazine | 35 |
| 0.050 mmol/l of Cu(II) dibutyldithiocarbamate | 205 |
| 0.050 mmol/l of Cu(II) oxine | >700 |
| 0.050 mmol/l of Cu(II) acetate* + 0.100 mmol/l of 8-aminoquinoline | >700 |
| 0.050 mmol/l of Cu(II) acetate* + 0.200 mmol/l of 1,1,4,7,10,10-hexamethyltriethylenetetramine | >700 |
| 0.050 mmol/l of Cu(II) acetate* + 0.200 mmol/l of Lupragen ® N205 | >700 |
| 0.050 mmol/l of Cu(II) acetate* + 0.200 mmol/l of Lupragen ® N600 | >700 |

*as monohydrate
**t denotes the time in minutes to polymerization

TABLE 5

Stabilization of acrylic esters

| Acrylic ester | Stabilizer | t** |
|---|---|---|
| 2-Ethylhexyl acrylate | 0.050 mmol/l of Cu(II) oxine | 364 |
| 2-Ethylhexyl acrylate | 0.050 mmol/l of Cu(II) acetate* + 0.100 mmol/l of 8 aminoquinoline | >700 |
| 2-Ethylhexyl acrylate | 0.050 mmol/l of Cu(II) acetate* + 0.200 mmol/l of 1,1,4,7,10,10-hexamethyltriethylenetetramine | 122 |
| 2-Ethylhexyl acrylate | 0.050 mmol/l of Cu(II) acetate* + 0.200 mmol/l of Lupragen ® N205 | 112 |
| 2-Ethylhexyl acrylate | 0.050 mmol/l of Cu(II) acetate* + 0.200 mmol/l of Lupragen ® N600 | 619 |
| Ethyl acrylate | 0.050 mmol/l of Cu(II) oxine | >700 |
| Ethyl acrylate | 0.050 mmol/l of Cu(II) acetate* + 0.100 mmol/l of 8-aminoquinoline | >700 |
| Ethyl acrylate | 0.050 mmol/l of Cu(II) acetate* + 0.200 mmol/l of 1,1,4,7,10,10-hexamethyltriethylenetetramine | >700 |
| Ethyl acrylate | 0.050 mmol/l of Cu(II) acetate* + 0.200 mmol/l of Lupragen ® N205 | >700 |
| Ethyl acrylate | 0.050 mmol/l of Cu(II) acetate* + 0.200 mmol/l of Lupragen ® N600 | >700 |
| Methyl acrylate | 0.050 mmol/l of Cu(II) oxine | >700 |
| Methyl acrylate | 0.050 mmol/l of Cu(II) acetate* + 0.100 mmol/l of 8-aminoquinoline | >700 |
| Methyl acrylate | 0.050 mmol/l of Cu(II) acetate* + 0.200 mmol/l of 1,1,4,7,10,10-hexamethyltriethylenetetramine | >700 |
| Methyl acrylate | 0.050 mmol/l of Cu(II) acetate* + 0.200 mmol/l of Lupragen ® N205 | >700 |
| Methyl acrylate | 0.050 mmol/l of Cu(II) acetate* + 0.200 mmol/l of Lupragen ® N600 | >700 |
| n-Butyl acrylate | 0.050 mmol/l of Cu(II) oxine | >700 |
| n-Butyl acrylate | 0.050 mmol/l of Cu(II) acetate* + 0.100 mmol/l of 8-aminoquinoline | >700 |
| tert-Butyl acrylate | 0.050 mmol/l of Cu(II) oxine | >700 |
| tert-Butyl acrylate | 0.050 mmol/l of Cu(II) acetate* + 0.100 mmol/l of 8-aminoquinoline | >700 |

*as monohydrate
**t denotes the time in minutes to polymerization

The invention claimed is:

1. A method of stabilizing acrylic compounds, comprising admixing a liquid phase comprising at least one acrylic compound selected from the group consisting of acrylic acid, methacrylic acid and a respective ester thereof with at least one metal selected from the group consisting of copper, manganese and cerium and also at least one ligand selected from the group consisting of quinoline compounds of formula (I):

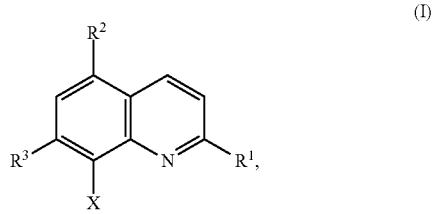

N-oxides of compounds of formula (I), 2,2'-bis(2,3-dihydro-3-oxoindolylidene), and aliphatic y-dentate ligands having y=2-6 and comprising at least two nitrogen atoms joined by aliphatic or aromatic $C_1$-$C_4$ bridges comprising y−2 further coordinating nitrogen atoms or heteroatoms, wherein X is OH, $NH_2$, O—$C_1$-$C_4$-alkyl, O—C(O)—$C_1$-$C_4$-alkyl, O—C(O)—$C_2H_5$ or O—C(O)-phenyl, $R^1$ is H, or ($C_1$-$C_4$)-alkyl, $R^2$ is H, $C_1$-$C_4$-alkyl, Cl, Br or $SO_3H$, and $R^3$ is H, Cl or Br.

2. The method according to claim 1, wherein a salt of the metal and the ligand are added to the liquid phase and a complex is formed in the liquid phase.

3. The method according to claim 1, wherein the metal is copper.

4. The method according to claim 3, wherein the metal is copper(II).

5. The method according to claim 2, wherein the metal salt is copper(II) acetate.

6. The method according to claim 1, wherein a content of metal in the liquid phase is from 0.01 mol to 5 mol %, based on the acrylic compound.

7. The method according to claim 1, wherein the ligand is at least one quinoline compound of formula (I) selected from the group consisting of 8-hydroxyquinoline, 8-hydroxy-5-methylquinoline, 5-chloroquinoline-8-yl propionate, 5-chloro-8-hydroxyquinoline, 5,7-dibromo-8-hydroxy-2-methylquinoline, 8-hydroxy-2-methylquinoline (8-hydroxyquinaldine), 8-acetoxyquinoline, 8-aminoquinoline, 8-amino-2-methylquinoline (8-aminoquinaldine), 5-amino-8-hydroxyquinoline and 8-hydroxyquinoline N-oxide.

8. The method according to claim 7, wherein the ligand is 8-hydroxyquinoline.

9. The method according to claim 1, wherein a molar ratio of metal to ligand is from 1:1 to 1:10.

10. The method according to claim 1, wherein the acrylic compound is acrylic acid.

11. The method according to claim 1, wherein

X is OH, $NH_2$, $OCH_3$, O—C(O)—$CH_3$, O—C(O)—$C_2H_5$ or O—C(O)-phenyl, $R^1$ is H, or methyl, $R^2$ is H, methyl, Cl, Br or $SO_3H$, and $R^3$ is H, Cl or Br.

* * * * *